(12) United States Patent
Hu et al.

(10) Patent No.: US 11,782,025 B2
(45) Date of Patent: Oct. 10, 2023

(54) METHOD FOR EVALUATING REMOVAL OF NITROGEN-CONTAINING ORGANIC MATTER IN WASTEWATER

(71) Applicant: Nanjing University, Nanjing (CN)

(72) Inventors: Haidong Hu, Nanjing (CN); Kewei Liao, Nanjing (CN); Jinfeng Wang, Nanjing (CN); Bing Wu, Nanjing (CN); Hongqiang Ren, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 372 days.

(21) Appl. No.: 17/219,878

(22) Filed: Mar. 31, 2021

(65) Prior Publication Data
US 2022/0136998 A1  May 5, 2022

(30) Foreign Application Priority Data
Nov. 4, 2020  (CN) .......................... 202011216523.1

(51) Int. Cl.
| | | |
|---|---|---|
| *G01N 27/623* | (2021.01) | |
| *G16C 20/70* | (2019.01) | |
| *B01D 11/04* | (2006.01) | |
| *G01N 1/34* | (2006.01) | |

(Continued)

(52) U.S. Cl.
CPC ....... *G01N 27/623* (2021.01); *B01D 11/0492* (2013.01); *G01N 1/34* (2013.01); *G16C 20/70* (2019.02); *C02F 1/58* (2013.01); *C02F 2101/38* (2013.01); *C02F 2209/16* (2013.01)

(58) Field of Classification Search
CPC ........ G01N 27/623; G01N 1/405; G01N 1/34; G01N 30/72; G01N 33/188; C02F 3/006
See application file for complete search history.

(56) References Cited

U.S. PATENT DOCUMENTS

2019/0154699 A1* 5/2019 Liebler .............. G01N 33/6848

FOREIGN PATENT DOCUMENTS

CN            111707739 A  *  9/2020

* cited by examiner

Primary Examiner — David E Smith
Assistant Examiner — Hsien C Tsai
(74) Attorney, Agent, or Firm — MATTHIAS SCHOLL P.C.; Matthias Scholl

(57) ABSTRACT

The disclosure provides a method for evaluation of removal of nitrogen-containing organic matter from the wastewater. The method includes: 1) pretreating a wastewater sample from a wastewater treatment plant; enriching nitrogen-containing organic matter in the wastewater sample with a solid-phase extraction cartridge; separating the nitrogen-containing organic matter from a substrate and disruptors of the wastewater sample, and collecting the nitrogen-containing organic matter; 2) detecting and analyzing the nitrogen-containing organic matter collected in 1) with a Fourier-transform ion cyclotron resonance mass spectrometer, thereby obtaining mass spectra of the nitrogen-containing organic matter; 3) preprocessing peak data of the mass spectra of the nitrogen-containing organic matter in each wastewater sample; setting the nitrogen-containing organic matter corresponding to the peak data as a global variable; arranging wastewater samples into cross-sectional data according to wastewater treatment processes; creating an assessment matrix for evaluating removal of the nitrogen-containing organic matter.

10 Claims, 1 Drawing Sheet

(51) Int. Cl.
*C02F 1/58* (2023.01)
*C02F 101/38* (2006.01)

METHOD FOR EVALUATING REMOVAL OF NITROGEN-CONTAINING ORGANIC MATTER IN WASTEWATER

CROSS-REFERENCE TO RELATED APPLICATIONS

Pursuant to 35 U.S.C. § 119 and the Paris Convention Treaty, this application claims foreign priority to Chinese Patent Application No. 202011216523.1 filed Nov. 4, 2020, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to the field of wastewater treatment, and more particularly, to a method for evaluating the removal of nitrogen-containing organic matter in wastewater.

Nitrogen-containing organic compounds from a wastewater treatment plant refer to various organic matter containing nitrogen functional groups, such as soluble nitrogen-containing organic matter, colloidal nitrogen-containing organic matter, and particulate nitrogen-containing organic matter.

In wastewater treatment processes, the colloidal nitrogen-containing organic matter and the particulate nitrogen-containing organic matter are removed by hydrolysis or converted into soluble nitrogen-containing organic matter. In this way, the soluble nitrogen-containing organic matter is the main nitrogen-containing organic substances in the wastewater treatment processes. The soluble nitrogen-containing organic matter exists in the treatment processes for wastewater. There are many types of soluble nitrogen-containing organic matter and their composition is complex, comprising organic compounds such as amino acids, amines, purines, nitriles, pyrimidines, and nitro compounds. Studies have shown that soluble nitrogen-containing organic matter can lead to membrane fouling during advanced wastewater treatment process and are the main precursors of nitrogenous disinfection by-products with high carcinogenicity. Removing the soluble nitrogen-containing organic matter may increase the capacity of wastewater treatment plants and improve effluent quality. Therefore, it is necessary to evaluate the effect of removal of the nitrogen-containing organic matter, mainly the soluble nitrogen-containing organics in wastewater treatment plants, so as to stabilize the operation of wastewater treatment plants and ensure the effluent quality.

Most of the existing evaluation methods use the macroscopic concentration of nitrogen-containing organics in the effluent of wastewater treatment plants as evaluation indicators, which cannot accurately determine the effect of removing nitrogen-containing organic matter from wastewater. Nitrogen-containing organic matter in wastewater treatment plants contains various nitrogen-containing organic matter molecules with different properties. Various nitrogen-containing organic molecules are replaced with a single macroscopic concentration to evaluate the sewage treatment capacity, ignoring the complex characteristics of nitrogen-containing organic matter and resulting in the loss of important information such as material change and pollutant composition. More importantly, the existing evaluation methods are used to evaluate the effect of removal of nitrogen-containing organic matter in a single wastewater treatment process of a wastewater treatment plant, and are rarely used to conduct a comprehensive and dynamic evaluation of the effect of removing the nitrogen-containing organic matter from the whole process of the wastewater treatment plant, resulting in lack of integrity and consistency in the evaluation results.

SUMMARY

The disclosure provides a method, based on high-resolution mass spectrometry and unsupervised dimensionality reduction techniques, for evaluation of removal of nitrogen-containing organic matter from the wastewater in different wastewater treatment processes, the method comprising:

1) pretreating a wastewater sample from a wastewater treatment plant; enriching nitrogen-containing organic matter in the wastewater sample with a solid-phase extraction cartridge; separating the nitrogen-containing organic matter from a substrate and disruptors of the wastewater sample through operations comprising column activation, sample loading, column rinsing, and column elution, and collecting the nitrogen-containing organic matter from the wastewater sample;

2) detecting and analyzing the nitrogen-containing organic matter collected in 1) with a Fourier-transform ion cyclotron resonance mass spectrometer, thereby obtaining mass spectra of the nitrogen-containing organic matter;

3) preprocessing peak data of the mass spectra of the nitrogen-containing organic matter in each wastewater sample; setting the nitrogen-containing organic matter corresponding to the peak data as a global variable; arranging wastewater samples into cross-sectional data according to wastewater treatment processes; creating an assessment matrix for evaluating removal of the nitrogen-containing organic matter from the wastewater treatment plant; inputting the assessment matrix into a statistical analysis software, thereby establishing an unsupervised dimensionality reduction analysis system;

4) homogenizing and standardizing global variables in the unsupervised dimensionality reduction analysis system; summarizing a correlation between two global variables with a multivariate statistical method; computing a covariance matrix of the global variables; and 5) calculating, based on the covariance matrix of the global variables, a score for estimating the removal of nitrogen-containing organic matter in the unsupervised dimensionality reduction analysis system corresponding to each wastewater treatment process; sorting scores in order; evaluating the effect of the removal of the nitrogen-containing organic matter from each wastewater treatment plant and each wastewater treatment process according to sorted scores.

In a class of this embodiment, the wastewater treatment plant is a municipal wastewater treatment plant or an industrial wastewater treatment plant; the wastewater treatment process comprises primary water treatment, secondary water treatment, and tertiary water treatment; when evaluating the effect of removal of nitrogen-containing organic matter, wastewater treatment processes of different wastewater treatment plants are of the same type. The method of the disclosure can simultaneously evaluate the effect of removal of the nitrogen-containing organic matter from each wastewater treatment process or a single wastewater treatment process of multiple wastewater treatment plants.

In a class of this embodiment, in 1), the wastewater sample is pretreated through a cellulose acetate membrane having a pore size of 0.45 μm to remove particles and bacteria, and a pH of the wastewater sample is adjusted to 2 with American Chemical Society (ACS)-grade high-purity hydrochloric acid. Higher extraction efficiency of nitrogen-containing organic matter can be obtained using the pre-treated wastewater sample. The solid-phase extraction cartridge is a commercial solid-phase extraction cartridge with styrene-divinylbenzene copolymer as a filler. Column activation comprises: removing the impurities in the solid-phase extraction cartridge with 2-3 times the column volume of LC-MS grade methanol, and equilibrating the solid-phase extraction cartridge with 3-5 times the column volume of ultrapure water acidified to pH 2. The wastewater sample is loaded onto the solid-phase extraction cartridge, with a flow rate of 0.5-2 mL/min. Column rinsing comprises: rinsing the solid-phase extraction cartridge loaded with the nitrogen-containing organics with 3 times the column volume of ultrapure water acidified to pH 2, blowing nitrogen into the solid-phase extraction cartridge to remove the remaining water, eluting the nitrogen-containing organics from the solid-phase extraction cartridge with 1-3 times the column volume of LC-MS grade methanol at a flow rate of 0.5-1.5 mL/min. Prior to analysis on an instrument, the concentration of dissolved organic carbon in the wastewater sample is measured to be 50-100 mg/L.

In a class of this embodiment, the ultrapure water acidified to pH 2 is LC-MS grade ultrapure water acidified by ACS grade high-purity hydrochloric acid. Note: some substances in the wastewater sample can be well adsorbed by the solid-phase extraction cartridge when the ultrapure water acidified to pH 2 is used, thereby obtaining an optimal extraction efficiency of nitrogen-containing organic matter in the wastewater sample.

In a class of this embodiment, in 2), the operating parameters for the Fourier-transform ion cyclotron resonance mass spectrometer are as follows: the mass spectrometer is equipped with an electrospray ionization source, operating in negative ion mode, at a sampling rate of 120-180 μL/h, a polarization voltage of 2.5-3.0 kV, a DC voltage of 2.2-2.4 V, and an accumulation time of 0.001-0.1 s. The mass of the collected molecules is in the range of 180-1000 Da and the number of sampling points is 2-4 M. The mass spectrum of the peak corresponding to the nitrogen-containing organic matter is a spectrum superimposed by 230-260 times. Note: Each operating parameter is controlled within the above given range to achieve the best peak detection and data analysis.

In a class of this embodiment, in 3), the data preprocessing is to calibrate the mass of nitrogen-containing organic matter that corresponds to peak in the mass spectrum according to the IUPAC calibration table, and the error range of the mass is ±1 ppm. A method for calculating the molecular formula of the nitrogen-containing organic matter that corresponds to the peak in the mass spectrum: processing the peak corresponding to the nitrogen-containing organic matter that has a signal-to-noise ratio greater than 6 with the high-resolution mass spectrometry software; calculating the molecular formula according to the ultra-high-precision mass-to-charge ratio of the peak corresponding to the nitrogen-containing organic matter. For each molecular formula, the number of carbon atoms is $2 \leq C \leq 50$, the number of hydrogen atoms is $2 \leq H \leq 120$ and $2 \leq H \leq 2C+2$, the number of oxygen atoms is $0 \leq O \leq 30$ and $0 \leq O \leq C+2$, the number of nitrogen atoms is $0 \leq N \leq 6$, $N<O$ and $N/C \leq 0.5$, the number of sulfur atoms is $0 \leq S \leq 2$, $S<O$ and $S/C \leq 0.2$, and the number of phosphorus atoms is $0 \leq P \leq 2$, $P/C \leq 0.1$ and $(2S+P)<O$, and the equivalent double bond is an integer greater than or equal to 0; the cross-sectional data is as follows: $G=\{W^t \in R^{n \times p}, t=1, 2, \ldots, T-1, T\}$, $W^t$ is the set of variables in t wastewater treatment processes of n wastewater treatment plants. $f_1, f_2, \ldots, f_n$ represent different wastewater treatment plants. $f_1^t, f_2^t, \ldots, f_n^t$ represent the set of molecular formulas of nitrogen-containing organic matter in the t process unit of different wastewater treatment plants. The intensities of the peaks corresponding to the molecular formulas of nitrogen-containing organic matter of the wastewater treatment plants are $e_1^t, e_2^t, \ldots, e_n^t$. The cluster point of the t wastewater treatment process of the wastewater treatment plant is $L^t=\{f_n^t, i=1, 2, \ldots, n\}$. The cluster point of the global sewage water sample is $L=U_{t=1}^T L^t$. The global molecular formulas of nitrogen-containing organic matter are as follows: $f_{1m}^1, \ldots, f_{nm}^1; f_{1m}^2, \ldots f_{nm}^2; \ldots; f_{1m}^t, \ldots, f_{nm}^t$.

In a class of this embodiment, the equivalent double bond is calculated as follows: equivalent double bond=C—H/2+N/2+1.

In a class of this embodiment, in 4), homogenizing comprises calculating a reciprocal of an inverse index; standardizing comprises calculating a standard deviation and logarithm of the intensities of the peaks corresponding to the molecular formula of all nitrogen-containing organic matter in the mass spectrum; the multivariate statistical method comprises Kaiser-Meyer-Olkin (KMO) test and Bartlett's test among variables; calculating the covariance matrix comprises homogenizing and globally standardizing the intensities of the peaks corresponding to the molecular formulas of the nitrogen-containing organic matter.

In a class of this embodiment, in 5), calculating the score for estimating the removal of nitrogen-containing organic matter comprises calculating eigenvalue, variance contribution rate of the eigenvalue, eigenvector, cumulative variance contribution rate, global principal components, and comprehensive score of each wastewater treatment plant; the eigenvalues, eigenvectors, variance contribution rate of the eigenvalues, cumulative variance contribution rate, and each global principal component are statistical parameters obtained after processing by an unsupervised dimensionality reduction analysis system that describe the effect of removal of nitrogen-containing organic matter in each wastewater treatment process. Note: the effect of removal of nitrogen-containing organic matter in multiple wastewater treatment plants and multiple processes is compared with the unsupervised dimensionality reduction, thereby obtaining the values of the statistical parameters. The score is calculated according to the statistical parameters and ordered by the simplest sorting method, thereby simplifying the complicated evaluation process. The statistical parameters can be used to evaluate the effect of removal of the nitrogen-containing organics in a complex system, which is also an advantage of unsupervised dimensionality reduction analysis techniques.

In a class of this embodiment, the global principal component should satisfy the condition that the eigenvalue is greater than 1; the score of each wastewater treatment process of each wastewater treatment plant is the sum of the product of the global principal component scores and their corresponding variance contribution rates.

The following advantages are associated with the method of the disclosure:

1) The disclosure provides a method for accurately evaluating the effect of removal of nitrogen-containing organics in the entire wastewater treatment process of multiple wastewater treatment plants.

2) The disclosure uses a mass spectrometer to characterize nitrogen-containing organic matter in each wastewater treatment process of a wastewater treatment plant, thus detecting nitrogen-containing organic matter in wastewater with ultra-high resolution and high-quality accuracy at the molecular level.

3) The disclosure employs the unsupervised dimensionality reduction technique to construct a data matrix for evaluating the effect of removal of nitrogen-containing organic matter in multiple wastewater treatment plants, and uses the multivariate statistical method to homogenize and standardize global variables, thereby improving the validity and comparability of the overall data.

BRIEF DESCRIPTION OF THE DRAWINGS

The invention is described hereinbelow with reference to accompanying drawings, in which the sole FIGURE is a flow chart of a method of evaluating the effect of removal of nitrogen-containing organic matter in wastewater treatment plants with high-resolution mass spectrometry in Example 1 of the disclosure.

DETAILED DESCRIPTION

To further illustrate the disclosure, embodiments detailing a method for evaluating the removal of nitrogen-containing organic matter in wastewater are described below. It should be noted that the following embodiments are intended to describe and not to limit the disclosure.

EXAMPLE 1

Figure 1:
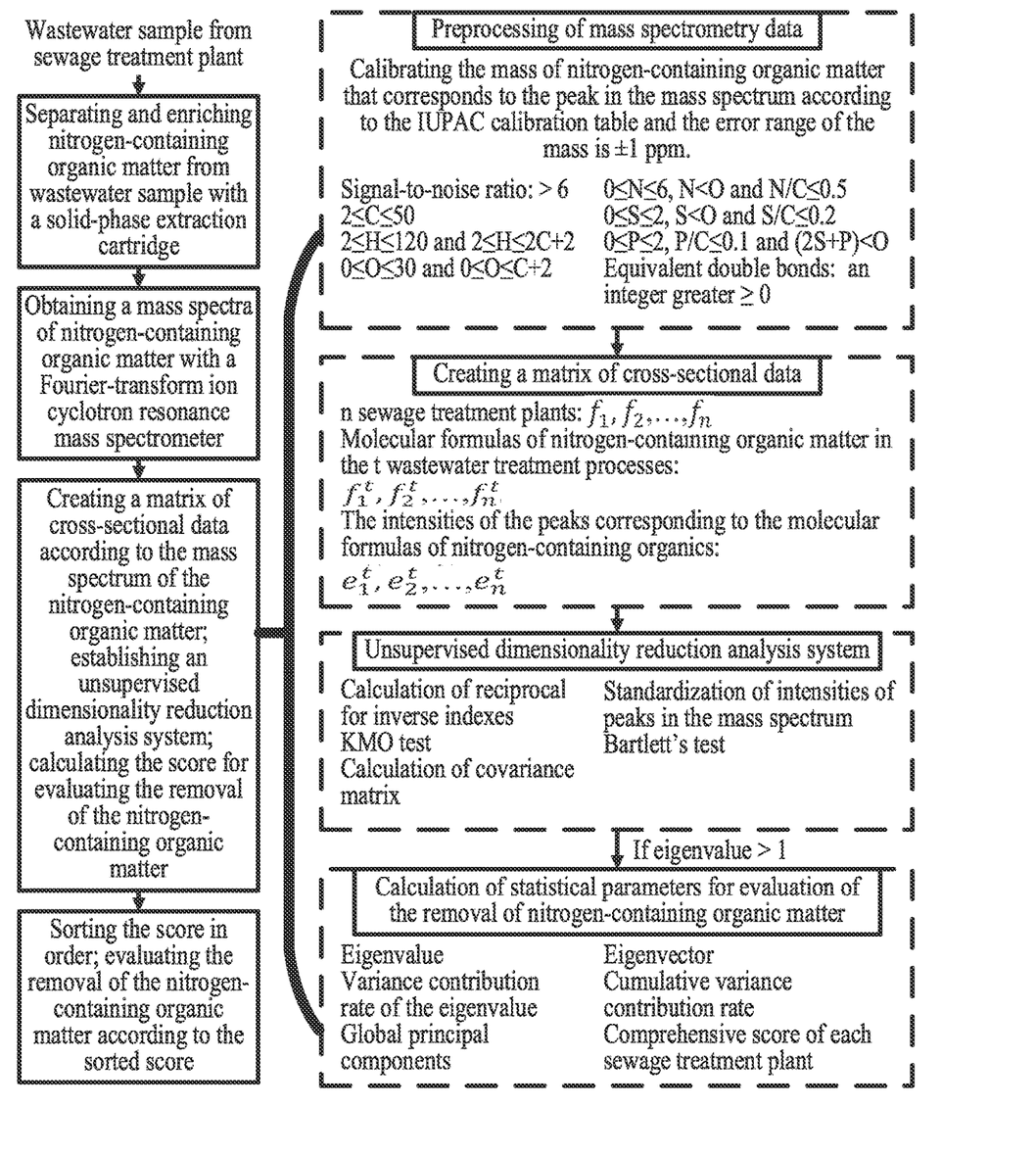

In Example 1, the effect of removal of nitrogen-containing organic matter in 6 municipal wastewater treatment plants in Jiangsu Province was evaluated. The 6 municipal wastewater treatment plants mainly adopted anaerobic/anoxic/aerobic processes. The wastewater samples were the influent from 6 municipal wastewater treatment plants, the effluent from each anaerobic/anoxic/aerobic process of the 6 municipal wastewater treatment plants, and the effluent from the 6 municipal wastewater treatment plants. The daily processing capacity of the 6 municipal wastewater treatment plants was as follows: wastewater treatment plant f1 was 43,800 cubic meters per day, wastewater treatment plant f2 was 61,300 cubic meters per day, wastewater treatment plant f3 was 3,200 cubic meters per day, and wastewater treatment plant f4 was 16,600 cubic meters per day, the wastewater treatment plant f5 was 6,800 cubic meters per day, and the wastewater treatment plant f6 was 38,100 cubic meters per day. FIG. 1 is a flow chart of evaluating the effect of removal of the nitrogen-containing organic matter in the 6 wastewater treatment plants with high-resolution mass spectrometry. The method based on high-resolution mass spectrometry and unsupervised dimensionality reduction techniques for evaluating the removal of nitrogen-containing organic matter in wastewater from different wastewater treatment processes is summarized as follows.

1) The wastewater sample collected from the wastewater treatment plant that was passed through a cellulose acetate membrane having the pore size of 0.45 μm, and then the pH of the wastewater sample was adjusted to 2 using ACS-grade high-purity hydrochloric acid. The solid-phase extraction cartridge was a commercial solid-phase extraction cartridge with styrene-divinylbenzene copolymer as a filler. The impurities in the solid-phase extraction cartridge were removed with 3 times the column volume of LC-MS grade methanol. The solid-phase extraction cartridge was equilibrated with 5 times the column volume of ultrapure water acidified to pH 2. The wastewater sample was loaded onto the solid-phase extraction cartridge, with a flow rate of 0.5 mL/min. The solid-phase extraction cartridge that had loaded the nitrogen-containing organic matter was rinsed with 3 times the column volume of ultrapure water acidified to pH 2. Nitrogen was blown into the solid-phase extraction cartridge to remove the remaining water. The nitrogen-containing organic matter was eluted from the solid-phase extraction cartridge with 2 times the column volume of LC-MS grade methanol at a flow rate of 0.5 mL/min. Prior to analysis on an instrument, the concentration of dissolved organic carbon in the wastewater sample was measured to be 50-100 mg/L.

2) The nitrogen-containing organic matter was detected and analyzed by a Fourier-transform ion cyclotron resonance mass spectrometer, thereby obtaining mass spectra of the nitrogen-containing organic matter. The operating parameters for the Fourier-transform ion cyclotron resonance mass spectrometer were as follows: the mass spectrometry was equipped with an electrospray ionization source, operated in negative ion mode, at a sampling rate of 120 μL/h, at a polarization voltage of 2.5 kV, at a DC voltage of 2.4 V, and using an accumulation time of 0.1 s. The mass of the collected molecules was in the range of 180-1000 Da and the number of sampling points was 2 M. The mass spectrum of the peak corresponding to the nitrogen-containing organic matter was a spectrum superimposed 230 times.

3) The mass of nitrogen-containing organic matter that corresponds to the peak in the mass spectrum was calibrated according to the IUPAC calibration table, and the error range of the mass was ±1 ppm. A method for calculating the molecular formula of the nitrogen-containing organic matter that corresponds to the peak in the mass spectrum: the peak corresponding to the nitrogen-containing organic matter that had a signal-to-noise ratio greater than 6 was processed with a high-resolution mass spectrometry software; each molecular formula was calculated according to the ultra-high-precision mass-to-charge ratio of the peak corresponding to the nitrogen-containing organic matter. For each molecular formula, the number of carbon atoms was $2 \leq C \leq 50$, the number of hydrogen atoms was $2 \leq H \leq 120$ and $2 \leq H \leq 2C+2$, the number of oxygen atoms was $0 \leq O \leq 30$ and $0 \leq O \leq C+2$, the number of nitrogen atoms was $0 \leq N \leq 6$, $N < O$ and $N/C \leq 0.5$, the number of sulfur atoms was $0 \leq S \leq 2$, $S < O$ and $S/C \leq 0.2$, and the number of phosphorus atoms was $0 \leq P \leq 2$, $P/C \leq 0.1$ and $(2S+P) < O$. The number of equivalent double bonds was an integer greater than or equal to 0 (The formula for calculating the equivalent double bond was as follows: equivalent double bond=C—H/2+N/2+1). The nitrogen-containing organic molecules after pretreatment were set as global variables. According to the wastewater treatment process, the wastewater samples were arranged into cross-sectional data $G=\{W^t \in R^{n \times p}, t=1, 2, \ldots, T-1, T\}$, $W^t$ was the set of variables in the 5 wastewater treatment processes of n wastewater treatment plants, comprising influent tank, anaerobic tank, anoxic tank, aerobic tank, and effluent tank. $f_1$, $f_2$, $f_3$, $f_4$, $f_5$, and $f_6$ represent different wastewater treatment plants. $f_1^t$, $f_2^t$, $f_3^t$, $f_4^t$, $f_5^t$, and $f_6^t$ represent the set of molecular formulas of nitrogen-containing organic matter in the t wastewater treatment processes of different wastewater treatment plants. The intensities of the peaks corresponding to the molecular formulas of nitrogen-containing organics of the different wastewater treatment plants were $e_1^t$, $e_2^t$, $e_3^t$, $e_4^t$, $e_5^t$, and $e_6^t$. The cluster point of the t wastewater treatment process of the wastewater treatment plant was $L^t = \{f_n^t, i=1, 2, \ldots, n\}$. The cluster point of the global wastewater sample was $L = U_{t=1}^T L^t$. The global molecular formulas of nitrogen-containing organic matter were as follows: $f_{1m}^1$, $f_{2m}^1$, $f_{3m}^1$, $f_{4m}^1$, $f_{5m}^1$, $f_{6m}^1$; $f_{1m}^2$, $f_{2m}^2$, $f_{3m}^2$, $f_{4m}^2$, $f_{5m}^2$, $f_{6m}^2$; $f_{1m}^t$, $f_{2m}^t$, $f_{3m}^t$, $f_{4m}^t$, $f_{5m}^t$, $f_{6m}^t$. As shown in Table 1, the cross-sectional data of nitrogen-containing organic matter in wastewater treatment plant f1 (There are 2289 molecular formula of nitrogen-containing organic matter, and 197 nitrogen-containing organic matters are listed in Table 1) was used to create an assessment matrix for evaluating the removal of nitrogen-containing organic matter in the effluent from the wastewater treatment plant. The assessment matrix was input into a statistical analysis software to establish an unsupervised dimensionality reduction analysis system.

4) The inverse index was homogenized with reciprocal method. Standard deviation and logarithm were used to standardize the intensities of the peaks in the mass spectrum that correspond to the molecular formulas of all nitrogen-containing organic matter. (Table 1 displayed the standardized cross-sectional data of the molecular formulas of nitrogen-containing organic matter). The Kaiser-Meyer-Olkin (KMO) test and Bartlett's test were used to determine the correlation between global variables in the unsupervised dimensionality reduction analysis system. The covariance matrix of the global variable was calculated using the standardized peak intensity of the nitrogen-containing organic molecules that are homogenized and globally standardized.

TABLE 1

197 nitrogen-containing organic matters in the cross-sectional data of the wastewater treatment plant f1 in Example 1

| Wastewater treatment plant | f1 | | | | |
| --- | --- | --- | --- | --- | --- |
| Formulas | Influent | Anaerobic tank | Anoxic tank | Aerobic tank | Effluent |
| C27 H24 N O15 S2 | −3.9485471 | −3.5286724 | −0.7215524 | −2.2838814 | −3.0667621 |
| C40 H16 N3 O4 S2 | −5 | −5 | −0.7215524 | −5 | −5 |
| C35 H70 N O8 | −1.8379301 | −1.8172201 | −2.038155 | −5 | −5 |
| C38 H67 N2 O5 | −1.8788049 | −5 | −5 | −5 | −5 |
| C31 H47 N2 O10 S2 | −2.2589911 | −2.2880925 | −2.2513948 | −2.984478 | −3.1479882 |
| C37 H74 N O8 | −2.2834924 | −2.2279797 | −2.21634 | −5 | −5 |
| C33 H66 N O8 | −2.1044256 | −2.2043427 | −2.5659407 | −5 | −5 |
| C17 H24 N O14 S | −1.874366 | −2.1577114 | −3.0514116 | −3.6749404 | −3.3021027 |
| C20 H41 N2 O4 | −2.7847871 | −2.7216829 | −2.84052 | −2.5430142 | −2.4796007 |
| C30 H43 N2 O15 | −2.2589911 | −2.2880925 | −2.2513948 | −2.984478 | −3.1479882 |
| C40 H71 N2 O5 | −5 | −5 | −2.6684524 | −5 | −5 |
| C34 H13 N2 O3 | −5 | −5 | −5 | −5 | −5 |
| C17 H33 N2 O16 S2 | −2.2459047 | −2.4393335 | −2.8940139 | −5 | −5 |
| C23 H24 N O20 S | −5 | −5 | −1.7972797 | −5 | −5 |
| C16 H31 N2 O16 S2 | −5 | −5 | −2.9040283 | −5 | −5 |
| C35 H15 N2 O3 | −5 | −5 | −5 | −5 | −5 |
| C36 H16 N3 O9 S | −5 | −5 | −1.7972797 | −5 | −5 |
| C36 H63 N2 O5 | −2.4064766 | −2.7041784 | −3.1145932 | −5 | −5 |
| C36 H17 N2 O3 | −2.7017591 | −2.7026227 | −2.8436665 | −2.6451456 | −2.6337075 |
| C35 H71 N2 O5 S | −2.3930678 | −2.424834 | −2.6685539 | −5 | −5 |
| C37 H26 N O11 S | −5 | −5 | −2.2171542 | −5 | −5 |
| C29 H30 N3 O13 S2 | −5 | −5 | −2.2171542 | −5 | −5 |
| C14 H18 N O14 | −2.3191166 | −2.6663976 | −3.5562529 | −3.4153823 | −3.1332863 |
| C33 H57 N2 O16 S2 | −3.6380941 | −3.6718498 | −5 | −2.6519978 | −2.578026 |
| C41 H27 N2 O3 | −2.6886263 | −2.7299838 | −3.2595654 | −2.8497985 | −2.8448913 |
| C38 H23 N2 O3 | −2.7274179 | −2.7526074 | −3.0251061 | −2.7810992 | −2.7447128 |
| C40 H23 N2 O4 | −2.7000363 | −2.7350025 | −3.2700064 | −2.852737 | −2.8589503 |
| C41 H25 N2 O3 | −2.7164711 | −2.7345217 | −3.295151 | −2.8931416 | −2.875073 |
| C37 H21 N2 O3 | −2.770464 | −2.7888933 | −2.9564985 | −2.7462093 | −2.7367574 |
| C32 H53 N2 O21 | −3.6380941 | −3.6718498 | −5 | −2.6519978 | −2.578026 |
| C40 H25 N2 O3 | −2.6653644 | −2.7339185 | −3.1869806 | −2.8504603 | −2.8023749 |
| C20 H30 N O14 S2 | −2.2642757 | −2.4822995 | −3.3956322 | −5 | −5 |
| C33 H15 N2 O3 | −2.9366735 | −2.9514622 | −5 | −5 | −5 |
| C34 H17 N2 O3 | −2.8128883 | −2.80381 | −2.912158 | −2.6972252 | −2.705608 |
| C39 H12 N3 O9 | −5 | −5 | −5 | −5 | −5 |
| C40 H25 N2 O4 | −2.706426 | −2.7328834 | −3.2806978 | −2.8549458 | −2.8503528 |
| C39 H25 N2 O3 | −2.7554751 | −2.8189171 | −3.1629516 | −2.8866719 | −2.8654531 |
| C43 H29 N2 O4 | −2.9406053 | −2.9028058 | −3.3159881 | −2.9129075 | −2.9910066 |
| C39 H23 N2 O3 | −2.6780787 | −2.730415 | −3.0808453 | −2.8062687 | −2.7859197 |
| C33 H67 N2 O5 S | −2.6802721 | −2.780958 | −3.1386686 | −5 | −5 |
| C37 H19 N2 O3 S | −5 | −5 | −5 | −5 | −5 |
| C41 H27 N2 O4 | −2.7667257 | −2.7843823 | −3.3650476 | −2.8774354 | −2.8858539 |
| C39 H21 N2 O8 | −2.6304312 | −2.5985358 | −3.5198194 | −3.5046624 | −3.5502999 |
| C38 H21 N2 O3 S | −5 | −5 | −5 | −5 | −5 |
| C42 H27 N2 O3 | −2.7612685 | −2.8060928 | −3.4050848 | −2.9449948 | −2.9310347 |
| C16 H18 N O9 | −2.9892996 | −3.0322014 | −3.1815104 | −2.9893332 | −3.0169459 |

TABLE 1-continued 197 nitrogen-containing organic matters in the cross-sectional data of the wastewater treatment plant f1 in Example 1

| Wastewater treatment plant | f1 | | | | |
|---|---|---|---|---|---|
| Formulas | Influent | Anaerobic tank | Anoxic tank | Aerobic tank | Effluent |
| C30 H14 N3 O24 | −5 | −3.9389159 | −3.8049397 | −5 | −5 |
| C38 H21 N2 O3 | −2.6506835 | −2.7063357 | −2.9615769 | −2.7355558 | −2.6801328 |
| C24 H26 N O17 S2 | −5 | −5 | −2.1410683 | −3.5704291 | −5 |
| C45 H14 N O4 S | −5 | −5 | −2.1410683 | −3.5704291 | −5 |
| C43 H14 N O12 S2 | −5 | −3.9389159 | −3.8049397 | −5 | −5 |
| C40 H21 N2 O4 | −2.8484506 | −2.866117 | −3.3772307 | −2.994757 | −3.009468 |
| C18 H26 N O14 S | −2.6900135 | −2.9519458 | −3.2684755 | −5 | −5 |
| C17 H18 N O10 | −3.0293631 | −3.0659977 | −3.2067027 | −3.0261819 | −3.0412762 |
| C42 H41 N2 O5 | −5 | −5 | −5 | −5 | −5 |
| C15 H18 N O9 | −3.0328584 | −3.0904095 | −3.2143593 | −3.0370347 | −3.0207363 |
| C32 H16 N3 O14 | −5 | −5 | −2.1810166 | −5 | −5 |
| C41 H23 N2 O3 | −2.8658792 | −2.9149021 | −3.4452014 | −3.0553693 | −3.0326385 |
| C17 H20 N O10 | −3.0255454 | −3.0422243 | −3.1901229 | −2.9606709 | −2.963934 |
| C15 H18 N O8 | −3.0741446 | −3.1070184 | −3.2729248 | −3.0143973 | −3.0738183 |
| C41 H29 N2 O3 | −2.8241431 | −2.8481937 | −3.3788767 | −2.950706 | −2.9585982 |
| C42 H27 N2 O4 | −2.8043473 | −2.7859907 | −3.3615916 | −2.8621716 | −2.8806687 |
| C54 H45 N2 O3 S | −5 | −5 | −5 | −5 | −5 |
| C39 H21 N2 O4 | −2.7128155 | −2.8125846 | −3.2557142 | −2.9084209 | −2.8787041 |
| C16 H20 N O9 | −3.0438401 | −3.0875384 | −3.2132872 | −3.0214364 | −3.033295 |
| C17 H18 N O9 | −3.1217913 | −3.1744415 | −3.3006167 | −3.0885224 | −3.0886302 |
| C43 H31 N2 O3 | −2.9067174 | −2.8850001 | −3.4492736 | −2.9644738 | −2.9657351 |
| C18 H20 N O11 | −3.0923 | −3.1189075 | −3.2690728 | −3.0795871 | −3.1030372 |
| C41 H23 N2 O4 | −2.843369 | −2.8806019 | −3.4910172 | −2.9960405 | −3.0052591 |
| C38 H21 N2 O4 | −2.7421759 | −2.8049228 | −3.1450922 | −2.8786439 | −2.8734256 |
| C42 H29 N2 O4 | −2.8552443 | −2.811631 | −3.362183 | −2.8703992 | −2.9070619 |
| C18 H20 N O10 | −3.0401085 | −3.0904034 | −3.2139276 | −3.0014398 | −3.0313981 |
| C37 H17 N2 O4 | −2.8198441 | −2.8798661 | −3.1473214 | −2.9030941 | −2.9064655 |
| C22 H24 N3 O17 S2 | −5 | −5 | −2.1804971 | −5 | −5 |
| C40 H23 N2 O8 | −2.9825289 | −3.0083286 | −3.1183527 | −3.444374 | −3.4917626 |
| C18 H20 N O9 | −3.1441866 | −3.2112268 | −3.2981688 | −3.081842 | −3.14017 |
| C18 H22 N O10 | −3.0646502 | −3.0836166 | −3.2286196 | −2.9837969 | −3.0012406 |
| C14 H16 N O9 | −3.0949414 | −3.1475654 | −3.2818251 | −3.1246822 | −3.0862114 |
| C15 H16 N O9 | −3.1166785 | −3.1418456 | −3.3181008 | −3.1406984 | −3.1167257 |
| C63 H51 N2 O4 S2 | −5 | −5 | −5 | −5 | −5 |
| C35 H13 N2 O4 | −3.0308823 | −3.0447283 | −3.1768296 | −2.9601267 | −2.9924865 |
| C42 H31 N2 O3 | −2.9510112 | −2.9569262 | −3.5441836 | −3.0625409 | −3.024039 |
| C15 H16 N O8 | −3.1015011 | −3.1476094 | −3.3068583 | −3.0986402 | −3.10676 |
| C37 H19 N2 O4 | −2.7564632 | −2.8214591 | −3.080591 | −2.8229482 | −2.8093065 |
| C40 H25 N2 O5 | −2.8923214 | −2.9001334 | −3.4603859 | −5 | −5 |
| C14 H16 N O8 | −3.10971 | −3.1732743 | −3.2909163 | −3.0933373 | −3.1071338 |
| C15 H20 N O9 | −3.094984 | −3.1652254 | −3.3057613 | −3.0838666 | −3.139254 |
| C17 H18 N O11 | −3.1268664 | −3.1957611 | −3.3434098 | −3.132153 | −3.148763 |
| C17 H20 N O8 | −3.1570593 | −3.1939194 | −3.3962081 | −3.1545036 | −3.1249865 |
| C36 H19 N O4 | −2.9248451 | −2.9712914 | −3.1461054 | −2.9106316 | −2.9113454 |
| C16 H16 N O9 | −3.1474881 | −3.1932177 | −3.3594182 | −3.1818668 | −3.1798666 |
| C16 H20 N O8 | −3.1646538 | −3.1843723 | −3.3552248 | −3.1069938 | −3.1111031 |
| C19 H22 N O11 | −3.193447 | −3.2525079 | −3.340282 | −5 | −3.20942 |
| C17 H20 N O9 | −3.1503216 | −3.1982432 | −3.3380011 | −3.130482 | −3.1476562 |
| C35 H65 N2 O27 S | −5 | −5 | −5 | −5 | −3.8485652 |
| C15 H20 N O8 | −3.2066302 | −3.2172881 | −3.3802901 | −3.1125593 | −3.1135344 |
| C56 H53 N2 O14 | −5 | −5 | −5 | −5 | −5 |
| C40 H21 N2 O3 | −2.8886118 | −2.9797093 | −3.4077852 | −3.0631563 | −3.0450585 |
| C16 H18 N O8 | −3.1857688 | −3.207874 | −3.3734588 | −3.1672644 | −3.1712503 |
| C18 H22 N O9 | −3.1213515 | −3.168642 | −3.3030759 | −3.0615589 | −3.0932891 |
| C15 H16 N O10 | −3.1355268 | −3.1876033 | −3.3002708 | −3.1914991 | −3.1864128 |
| C43 H29 N2 O3 | −2.8897627 | −2.8598731 | −3.4530845 | −2.9679966 | −2.961526 |
| C19 H40 N O7 | −2.4481876 | −5 | −5 | −3.7192064 | −5 |
| C23 H43 N2 O18 S | −3.0822586 | −3.0039268 | −3.1607716 | −2.9181266 | −5 |
| C22 H41 N2 O17 S | −2.9406053 | −2.9028058 | −3.3159881 | −2.9129075 | −2.9910066 |
| C20 H39 N2 O16 S | −2.6886263 | −2.7299838 | −3.2595654 | −2.8497985 | −2.8448913 |
| C52 H56 N O8 S2 | −3.448048 | −3.5606772 | −3.8605152 | −2.7287363 | −2.6897487 |
| C14 H18 N O8 | −3.2018826 | −3.245624 | −3.4052982 | −3.1831183 | −3.1567141 |
| C35 H19 N2 O3 | −2.9128435 | −2.8628535 | −2.9631289 | −2.7553765 | −2.7622711 |
| C22 H39 N2 O19 S | −3.1403526 | −3.0518428 | −3.2329683 | −2.9522815 | −3.0140865 |
| C16 H22 N O9 | −3.249126 | −3.2294098 | −3.3529148 | −3.1618294 | −3.1600862 |
| C37 H17 N2 O3 | −2.8632057 | −2.9016156 | −3.0450503 | −2.870452 | −2.8419296 |
| C19 H22 N O10 | −5 | −5 | −3.3801346 | −5 | −5 |
| C17 H22 N O8 | −3.2077508 | −3.2392841 | −3.4037155 | −3.1596831 | −3.1600028 |
| C38 H19 N2 O5 | −2.8618889 | −2.9339648 | −3.4091528 | −3.0362543 | −3.0012933 |
| C21 H32 N O14 S2 | −2.7363977 | −2.9165365 | −5 | −5 | −5 |
| C19 H22 N O9 | −3.2828407 | −3.3392899 | −3.4450611 | −3.2348247 | −3.2665425 |
| C20 H26 N O10 | −3.2281424 | −3.191935 | −3.32271 | −2.9800637 | −2.9869906 |

TABLE 1-continued 197 nitrogen-containing organic matters in the cross-sectional data of the wastewater treatment plant f1 in Example 1

| Wastewater treatment plant | f1 | | | | |
|---|---|---|---|---|---|
| Formulas | Influent | Anaerobic tank | Anoxic tank | Aerobic tank | Effluent |
| C14 H16 N O7 | −3.2598423 | −3.2784536 | −3.4282705 | −3.1725519 | −3.1848656 |
| C16 H18 N O10 | −3.1526076 | −3.2515808 | −3.4073648 | −3.2046898 | −3.2511931 |
| C41 H29 N2 O4 | −2.9708934 | −2.9453992 | −3.4894641 | −3.0216923 | −3.0496767 |
| C14 H18 N O9 | −3.2245468 | −3.2604951 | −3.412391 | −3.2432012 | −3.2375868 |
| C21 H26 N O11 | −3.3054131 | −3.3264474 | −3.4435971 | −5 | −5 |
| C45 H33 N2 O5 | −5 | −5 | −3.1381324 | −2.9840988 | −2.9954612 |
| C35 H13 N2 O3 | −2.9642998 | −2.9746758 | −5 | −2.8896005 | −2.8915744 |
| C21 H37 N2 O18 S | −2.9850182 | −2.947436 | −3.3837366 | −2.9242004 | −3.0197787 |
| C34 H43 N2 O10 S | −2.526676 | −2.616258 | −3.0499452 | −3.6381287 | −5 |
| C43 H44 N O3 S | −2.8197114 | −2.8779953 | −2.968202 | −5 | −5 |
| C18 H22 N O8 | −3.2441666 | −3.2831659 | −3.4321715 | −3.1965189 | −3.1997911 |
| C14 H14 N O8 | −3.2128684 | −3.2900911 | −3.4644845 | −3.2534307 | −3.2579132 |
| C50 H39 N2 O3 S2 | −5 | −3.2218803 | −3.4721416 | −3.3283412 | −3.3632747 |
| C24 H43 N2 O19 S | −3.1159803 | −3.1099781 | −3.1824815 | −2.9961983 | −3.0107073 |
| C18 H24 N O9 | −3.2762877 | −3.2664107 | −3.3996484 | −3.1419676 | −3.1308509 |
| C15 H18 N O7 | −3.2557549 | −3.3000685 | −3.4659684 | −3.2012881 | −3.1848186 |
| C13 H14 N O8 | −3.2152121 | −3.3027875 | −3.5065056 | −3.1702926 | −3.2302289 |
| C18 H20 N O8 | −3.2465454 | −3.286074 | −3.4764451 | −3.2437502 | −3.2004433 |
| C42 H25 N2 O4 | −2.8742895 | −2.8620494 | −3.4502072 | −2.9464353 | −2.9803469 |
| C40 H19 N2 O4 | −3.0554705 | −3.0852888 | −3.627817 | −3.2363267 | −3.2035742 |
| C20 H37 N2 O19 S | −3.0590934 | −3.0016663 | −3.4110618 | −2.9362152 | −3.0169893 |
| C14 H18 N O7 | −3.3165478 | −3.3378723 | −3.4920544 | −3.2523611 | −3.2532497 |
| C39 H27 N2 O4 | −3.0963092 | −3.1592095 | −3.573641 | −3.2339914 | −3.1913648 |
| C46 H33 N2 O4 | −3.1862596 | −3.1288884 | −3.1890101 | −3.0414339 | −3.0844515 |
| C20 H24 N O11 | −3.2627039 | −3.2797923 | −3.3472811 | −3.1783427 | −3.1707653 |
| C36 H17 N2 O4 | −2.8783857 | −2.9077337 | −3.0716261 | −2.8834325 | −2.8584275 |
| C46 H33 N2 O3 S2 | −3.3239273 | −3.3713 | −3.4980191 | −3.2949187 | −3.3200409 |
| C47 H35 N2 O3 S2 | −5 | −3.2713362 | −3.4557295 | −5 | −5 |
| C21 H26 N O13 | −3.3642048 | −3.3084906 | −3.4480166 | −3.2051432 | −3.2075225 |
| C44 H33 N2 O3 | −3.138741 | −3.0479862 | −3.5029829 | −3.0805207 | −3.1609944 |
| C19 H33 N2 O17 S | −2.8484506 | −2.866117 | −3.3772307 | −2.994757 | −3.009468 |
| C13 H14 N O7 | −3.2928962 | −3.3211677 | −3.5359578 | −3.2188574 | −3.2152166 |
| C13 H16 N O7 | −3.2941566 | −3.3274757 | −3.5277392 | −3.2380262 | −3.213682 |
| C19 H35 N2 O17 S | −2.7000363 | −2.7350025 | −3.2700064 | −2.852737 | −2.8589503 |
| C48 H35 N2 O3 S2 | −3.2509217 | −3.2512281 | −3.5684357 | −3.3711756 | −3.4137583 |
| C49 H37 N2 O3 S2 | −3.2718233 | −3.2294537 | −3.5269022 | −3.3691454 | −3.3775561 |
| C17 H22 N O9 | −3.2471283 | −3.2935295 | −3.4197821 | −3.1986538 | −3.2631608 |
| C45 H35 N2 O4 | −3.2369622 | −3.1647985 | −3.31849 | −3.0656805 | −3.1263496 |
| C14 H28 N O14 S2 | −2.3284503 | −5 | −5 | −3.8342806 | −3.7428174 |
| C21 H24 N O13 | −3.3715107 | −3.3644813 | −3.43326 | −3.2423783 | −3.2534355 |
| C19 H24 N O9 | −3.337794 | −3.3540837 | −3.4507493 | −3.2167508 | −3.2641637 |
| C50 H41 N2 O3 S2 | −5 | −5 | −3.4597749 | −3.2897112 | −3.2956786 |
| C23 H41 N2 O19 S | −3.1048585 | −3.102682 | −3.1509774 | −2.9575012 | −2.9897343 |
| C17 H25 N2 O11 S2 | −2.6159032 | −2.8422921 | −5 | −5 | −5 |
| C51 H41 N2 O3 S2 | −5 | −5 | −3.4738921 | −3.2746859 | −5 |
| C17 H16 N O9 | −3.3075965 | −3.3383239 | −3.5312374 | −3.2969834 | −3.3179185 |
| C13 H16 N O8 | −3.280361 | −3.3101971 | −3.5169074 | −3.2971967 | −3.2537751 |
| C51 H39 N2 O3 S2 | −3.3164391 | −3.283638 | −3.5422967 | −3.3552285 | −3.3767375 |
| C18 H18 N O9 | −3.2640921 | −3.3143374 | −3.4438675 | −3.2435224 | −3.2380784 |
| C13 H16 N O6 | −3.4516109 | −3.4677339 | −3.6022314 | −3.3653286 | −3.3847937 |
| C37 H15 N2 O3 | −3.1203615 | −3.1454549 | −3.3159839 | −3.0864668 | −3.0835315 |
| C20 H37 N2 O16 S | −2.7164711 | −2.7345217 | −3.295151 | −2.8931416 | −2.875073 |
| C38 H23 N2 O5 | −3.0314512 | −3.0943542 | −3.5698466 | −5 | −3.145838 |
| C34 H20 N O10 S2 | −5 | −5 | −2.3451951 | −5 | −5 |
| C51 H43 N2 O3 S2 | −5 | −5 | −3.4812908 | −3.2952929 | −3.3379674 |
| C21 H24 N O12 | −3.2923417 | −3.2855502 | −3.445131 | −3.1697889 | −3.1957191 |
| C20 H24 N O9 | −3.3497692 | −3.3810202 | −3.4890927 | −3.2971128 | −3.2972176 |
| C16 H20 N O7 | −3.2862207 | −3.3167656 | −3.4792253 | −3.2791523 | −3.2571902 |
| C14 H14 N O9 | −3.2857962 | −3.3326374 | −3.4768559 | −3.3317844 | −3.3211705 |
| C43 H33 N2 O3 | −3.0834329 | −3.0535861 | −3.6335263 | −3.0968063 | −3.121875 |
| C37 H59 N2 O27 | −5 | −5 | −5 | −5 | −5 |
| C39 H19 N2 O5 | −2.8924149 | −2.9556637 | −3.4897784 | −5 | −5 |
| C37 H19 N2 O3 | −2.7561561 | −2.7560699 | −2.9433305 | −2.7352023 | −2.7122364 |
| C21 H39 N2 O16 S | −2.7612685 | −2.8060928 | −5 | −2.9449948 | −2.9310347 |
| C45 H31 N2 O3 S2 | −3.3790206 | −3.4068854 | −3.5411655 | −3.3386734 | −3.3140093 |
| C16 H16 N O8 | −3.3045398 | −3.3793848 | −3.5327788 | −3.299088 | −3.3314465 |
| C19 H22 N O12 | −5 | −5 | −5 | −5 | −5 |
| C46 H33 N2 O7 | −3.1727601 | −3.1818509 | −3.3290051 | −3.1903995 | −3.2010794 |
| C43 H33 N2 O4 | −3.2250157 | −3.1507928 | −3.5819254 | −3.0758398 | −3.1531009 |
| C43 H29 N2 O5 | −3.150762 | −3.1056998 | −3.4655461 | −5 | −3.1640572 |
| C17 H18 N O8 | −3.3577281 | −3.3538049 | −3.5386907 | −3.3157615 | −3.3020962 |
| C16 H16 N O10 | −3.2804625 | −3.3322751 | −3.4733633 | −3.3137384 | −3.2966413 |

TABLE 1-continued 197 nitrogen-containing organic matters in the cross-sectional data of the wastewater treatment plant f1 in Example 1

| Wastewater treatment plant | f1 | | | | |
|---|---|---|---|---|---|
| Formulas | Influent | Anaerobic tank | Anoxic tank | Aerobic tank | Effluent |
| C50 H39 N2 O4 S2 | −5 | −3.2966429 | −3.4924592 | −3.2992246 | −3.4165521 |
| C29 H16 N3 O21 | −5 | −3.9485288 | −3.1541339 | −5 | −5 |
| C37 H23 N2 O4 | −3.113446 | −3.1397293 | −3.4013717 | −3.1104973 | −3.1180935 |
| C39 H23 N2 O4 | −2.6968384 | −2.7832212 | −3.2146893 | −2.8673997 | −2.8302358 |
| C16 H16 N O11 | −3.3254613 | −3.3758368 | −3.5047982 | −3.3096481 | −3.3217922 |
| C44 H29 N2 O3 | −3.0865672 | −3.0168384 | −3.4865119 | −3.0568263 | −3.097274 |
| C21 H39 N2 O19 S | −3.1222996 | −3.0631253 | −3.3246443 | −2.9588915 | −3.0119719 |

5) The covariance matrix of global variables was used to calculate the eigenvalues, variance contribution rate of the eigenvalues, eigenvectors, cumulative variance contribution rate, global principal components, and comprehensive score of each wastewater treatment process of each wastewater sewage plant (The global principal component should satisfy the condition that the eigenvalue was greater than 1). A score for the removal of nitrogen-containing organic matter in each wastewater treatment process was calculated with the unsupervised feature reduction technique. The score for the removal of nitrogen-containing organic matter from each wastewater treatment process of the wastewater treatment plant was calculated according to the sum of the product of the score of each wastewater treatment process in each global principal component and the contribution rate of the corresponding variance. The score is sorted in order, thereby evaluating the effect of removal of the nitrogen-containing organic matter in each wastewater treatment plant and each wastewater treatment process.

TABLE 2

Score and rank of removal of nitrogen-containing organic matter in the influent and effluent from wastewater treatment plants

| Municipal wastewater treatment plant | Influent | | Anaerobic tank | | Anoxic tank | | Aerobic tank | | Effluent | |
|---|---|---|---|---|---|---|---|---|---|---|
| | Score | Rank | Score | Rank | Score | Rank | Score | Rank | Score | Rank |
| f1 | 1.054 | 2 | 1.084 | 1 | 0.335 | 2 | −0.413 | 4 | 1.388 | 1 |
| f2 | 0.009 | 4 | 0.377 | 2 | −1.117 | 6 | 1.392 | 1 | 0.297 | 3 |
| f3 | 1.231 | 1 | −1.077 | 6 | 0.382 | 1 | −0.802 | 6 | 0.241 | 4 |
| f4 | −0.110 | 5 | −0.368 | 4 | 0.170 | 4 | 0.142 | 2 | 0.471 | 2 |
| f5 | −0.315 | 6 | 0.045 | 3 | 0.267 | 3 | 0.103 | 3 | −1.097 | 6 |
| f6 | 0.407 | 3 | −0.433 | 5 | −0.082 | 5 | −0.457 | 5 | −0.138 | 5 |

The effect of removal of nitrogen-containing organic matter was ranked and evaluated by score. The scores in Table 2 were calculated using the molecular composition of nitrogen-containing organic matter in the wastewater and the matrix of intensities of peaks corresponding to the nitrogen-containing organic matter. The higher the score, the higher the rank, and the more the serious pollution/the worse the removal effect caused by the nitrogen-containing organic matter in the wastewater. In the 6 municipal domestic wastewater treatment plants, the pollution degree of nitrogen-containing organic matter in the influent: f3>f1>f6>f2>f4>f5; the effect of removal of nitrogen-containing organic matter from the anaerobic tank: f3>f6>f4>f5>f2>f1; the effect of removal of nitrogen-containing organic matter from the anoxic rank: f2>f6>f4>f5>f1>f3; the effect of removal of nitrogen-containing organic matter from the aerobic tank: f3>f6>f1>f5>f4>f2; the contribution rate of nitrogen-containing organic matter was defined as the standard, and the cleanliness of the effluent was ranked as f5>f6>f3>f2>f4>f1. According to the ranking, the removal effect of nitrogen-containing organic matter in the municipal wastewater treatment plant f1 was lower than that of other wastewater treatment plants. The effect of removal of nitrogen-containing organic matter in the municipal wastewater treatment plant f3 was better than that of other wastewater treatment plants.

EXAMPLE 2

In Example 2, the effect of removal of nitrogen-containing organic matter in 5 municipal wastewater treatment plants in the Pearl River Delta was evaluated. The 5 municipal wastewater treatment plants adopt oxidation ditch processes. The wastewater samples were the influent from 5 municipal wastewater treatment plants, the effluent from oxidation ditch processes of the 5 municipal wastewater treatment plants, and the effluent from the wastewater treatment plant. The daily processing capacity of the 5 municipal wastewater treatment plants was as follows: wastewater treatment plant f1 is 47,600 cubic meters per day, wastewater treatment plant f2 is 44,000 cubic meters per day, wastewater treatment plant f3 is 84,300 cubic meters per day, and wastewater treatment plant f4 is 4,200 cubic meters per day, and the wastewater treatment plant f5 is 26,300 cubic meters per day. A method based on high-resolution mass spectrometry and unsupervised dimensionality reduction techniques for evaluating the removal of nitrogen-containing organic matter from wastewater in different wastewater treatment processes, comprises:

1) The wastewater sample collected from the wastewater treatment plant that was passed through a cellulose acetate membrane having the pore size of 0.45 μm, and then the pH of the wastewater sample was adjusted to 2 using ACS-grade high-purity hydrochloric acid. The solid-phase extraction cartridge was a commercial solid-phase extraction cartridge with styrene-divinylbenzene copolymer as a filler. The impurities in the solid-phase extraction cartridge were removed with 2 times of column volume of LC-MS grade methanol. The solid-phase extraction cartridge was equilibrated with 4 times the column volume of ultrapure water acidified to pH 2. The wastewater sample was loaded onto the solid-phase extraction cartridge, with a flow rate of 1.0 mL/min. The solid-phase extraction cartridge that had loaded the nitrogen-containing organic matter was rinsed with 4 times the column volume of ultrapure water acidified to pH 2. Nitrogen was blown into the solid-phase extraction cartridge to remove the remaining water. The nitrogen-containing organic matter was eluted from the solid-phase extraction cartridge with 2 times the column volume of LC-MS grade methanol at a flow rate of 1.0 mL/min. Prior to analysis on an instrument, the concentration of dissolved organic carbon in the wastewater sample was measured to be 50-100 mg/L.

2) The nitrogen-containing organic matter was detected and analyzed by a Fourier-transform ion cyclotron resonance mass spectrometer; thereby obtaining mass spectra of the nitrogen-containing organic matter. The operating parameters for the Fourier-transform ion cyclotron resonance mass spectrometer were as follows: the mass spectrometry was equipped with an electrospray ionization source, operated in negative ion mode, at a sampling rate of 150 μL/h, at a polarization voltage of 2.7 kV, at a DC voltage of 2.3 V, and using an accumulation time of 0.1 s. The mass of the collected molecules was in the range of 180-1000 Da and the number of sampling points was 4 M. The mass spectrum of the peak corresponding to the nitrogen-containing organic matter was a spectrum superimposed 250 times.

3) The mass of nitrogen-containing organic matter that corresponds to the peak in the mass spectrum was calibrated according to the IUPAC calibration table, and the error range of the mass was ±1 ppm. A method for calculating the molecular formula of the nitrogen-containing organic matter that corresponds to the peak in the mass spectrum: the peak corresponding to the nitrogen-containing organic matter that had a signal-to-noise ratio greater than 6 was processed with a high-resolution mass spectrometry software; the molecular formula was calculated according to the ultra-high-precision mass-to-charge ratio of the peak corresponding to the nitrogen-containing organic matter. For each molecular formula, the number of carbon atoms was $2 \leq C \leq 50$, the number of hydrogen atoms was $2 \leq H \leq 120$ and $2 \leq H \leq 2C+2$, the number of oxygen atoms was $0 \leq O \leq 30$ and $0 \leq O \leq C+2$, the number of nitrogen atoms was $0 \leq N \leq 6$, $N<O$ and $N/C \leq 0.5$, the number of sulfur atoms was $0 \leq S \leq 2$, $S<O$ and $S/C \leq 0.2$, and the number of phosphorus atoms was $0 \leq P \leq 2$, $P/C \leq 0.1$ and $(2S+P)<O$. The number of equivalent double bonds is an integer greater than or equal to 0 (The formula for calculating the equivalent double bond was as follows: equivalent double bond=C—H/2+N/2+1). The nitrogen-containing organic molecules after pretreatment were set as global variables. According to the wastewater treatment process, the wastewater samples were arranged into cross-sectional data $G=\{W^t \in R^{n \times p}, t=1, 2, \ldots, T-1, T\}$, $W^t$ was the set of variables in the 5 wastewater treatment processes of n wastewater treatment plants, comprising influent tank, anoxic tank, aerobic tank, and effluent tank. $f_1$, $f_2$, $f_3$, $f_4$, $f_5$, and $f_6$ represent different wastewater treatment plants. $f_1^t$, $f_2^t$, $f_3^t$, $f_4^t$, $f_5^t$, and $f_6^t$ represent the set of molecular formulas of nitrogen-containing organic matter in the t wastewater treatment processes of different wastewater treatment plants. The intensities of the peaks corresponding to the molecular formulas of nitrogen-containing organics of the wastewater treatment plants are $e_1^t$, $e_2^t$, $e_3^t$, $e_4^t$, $e_5^t$, and $e_6^t$. The cluster points of the t wastewater treatment processes of the wastewater treatment plant was represented by $L^t=\{f_n^t, i=1, 2, \ldots, n\}$. The cluster points of the global sewage water sample were represented by $L=U_{t=1}^T L^t$. The global molecular formulas of nitrogen-containing organic matter were as follows. $f_{1m}^1$, $f_{2m}^1$, $f_{3m}^1$, $f_{4m}^1$, $f_{5m}^1$; $f_{1m}^2$, $f_{2m}^2$, $f_{3m}^2$, $f_{4m}^2$, $f_{5m}^2$; $f_{1m}^t$, $f_{2m}^t$, $f_{3m}^t$, $f_{4m}^t$, $f_{5m}^t$. The cross-sectional data was used to create an assessment matrix for evaluating the removal of nitrogen-containing organic matter in the effluent from the wastewater treatment plant. The assessment matrix was input into a statistical analysis software to establish an unsupervised dimensionality reduction analysis system.

4) The inverse index was homogenized with the reciprocal method. Standard deviation and logarithm were used to standardize the intensities of the peaks in the mass spectrum that correspond to the molecular formulas of all nitrogen-containing organic matter. The Kaiser-Meyer-Olkin (KMO) test and Bartlett's test were used to determine the correlation between global variables in the unsupervised dimensionality reduction analysis system. The covariance matrix of the global variable was calculated using the standardized peak intensity of the nitrogen-containing organic molecules that are homogenized and globally standardized.

5) The covariance matrix of global variables was used to calculate the eigenvalues, variance contribution rate of the eigenvalues, eigenvectors, cumulative variance contribution rate, global principal components, and comprehensive score of each wastewater treatment process of each wastewater sewage plant (The global principal component should satisfy the condition that the eigenvalue was greater than 1). A score for the removal of nitrogen-containing organic matter in each wastewater treatment process was calculated with the unsupervised feature reduction technique. The score for the removal of nitrogen-containing organic matter from each wastewater treatment process of the wastewater treatment plant was calculated according to the sum of the product of the score of each wastewater treatment process in each global principal component and the contribution rate of the corresponding variance. The score is sorted in order, thereby evaluating the effect of removal of the nitrogen-containing organic matter in each wastewater treatment plant and each wastewater treatment process.

TABLE 3

Score and rank of the removal effect of nitrogen-containing organic matter in the influent and effluent of wastewater treatment plants

| Municipal wastewater treatment plant | Influent | | Aerobic tank | | Effluent | |
|---|---|---|---|---|---|---|
| | Score | Rank | Score | Rank | Score | Rank |
| f1 | 1.387 | 1 | 0.578 | 3 | 0.768 | 1 |
| f2 | 0.435 | 3 | 1.208 | 1 | −0.092 | 4 |
| f3 | −1.2529 | 5 | 0.819 | 2 | −1.006 | 5 |
| f4 | −0.868 | 4 | −0.506 | 4 | 0.644 | 2 |
| f5 | 0.9486 | 2 | −1.034 | 5 | 0.582 | 3 |

The effect of removal of nitrogen-containing organic matter is ranked and evaluated by score. The scores in Table 3 were calculated using the molecular composition of nitrogen-containing organic matter in the wastewater and the matrix of peak intensity corresponding to the nitrogen-containing organic matter. The higher the score, the higher the rank, and the more the serious pollution/the worse the removal effect caused by the nitrogen-containing organic matter in the wastewater. In the 5 municipal domestic wastewater treatment plants, the pollution degree of nitrogen-containing organic matter in the influent. f1>f5>f2>f4>f3; the removal effect of nitrogen-containing organic matter in the oxidation ditch: f5>f4>f1>f3>f2; the contribution rate of nitrogen-containing organic matter was defined as the standard, and the cleanliness of the effluent was ranked as f3>f2>f5>f4>f1. According to the ranking, the removal effect of nitrogen-containing organic matter in the municipal wastewater treatment plant f1 was lower than that of other wastewater treatment plants. The removal effect of nitrogen-containing organic matter in the oxidation ditch of the municipal wastewater treatment plant f5 was better than that of other wastewater treatment processes of other wastewater treatment plants. The effect of removal of nitrogen-containing organic matter in the municipal wastewater treatment plant f3 was more stable than that of other wastewater treatment plants.

EXAMPLE 3

In Example 3, the effect of removal of nitrogen-containing organic matter in 7 municipal wastewater treatment plants in Jiangsu Province was evaluated. The 7 municipal wastewater treatment plants adopt anaerobic/anoxic/aerobic processes. The wastewater samples were the influent from 7 municipal domestic wastewater treatment plants, the effluent from each anaerobic/aerobic process of the 7 municipal domestic wastewater treatment plants, and the effluent from the wastewater treatment plant. The daily processing capacity of the 7 municipal wastewater treatment plants was as follows: wastewater treatment plant f1 was 10,100 cubic meters per day, wastewater treatment plant f2 was 44,400 cubic meters per day, wastewater treatment plant f3 was 13,700 cubic meters per day, and wastewater treatment plant f4 was 7,100 cubic meters per day, the wastewater treatment plant f5 was 14,600 cubic meters per day, the wastewater treatment plant f6 is 1,600 cubic meters per day, and the wastewater treatment plant f7 is 36,000 cubic meters per day. A method based on high-resolution mass spectrometry and unsupervised dimensionality reduction techniques for evaluation of removal of nitrogen-containing organic matter in wastewater treated in different wastewater treatment processes, comprising:

1) The wastewater sample collected from the wastewater treatment plant that was passed through a cellulose acetate membrane having the pore size of 0.45 μm, and the pH of the wastewater sample was adjusted to 2 using ACS-grade high-purity hydrochloric acid. The solid-phase extraction cartridge was a commercial solid-phase extraction cartridge with styrene-divinylbenzene copolymer as a filler. The impurities in the solid-phase extraction cartridge were removed with 3 times the column volume of LC-MS grade methanol. The solid-phase extraction cartridge was equilibrated with 5 times the column volume of ultrapure water acidified to pH 2. The wastewater sample was loaded onto the solid-phase extraction cartridge, with a flow rate of 2 mL/min. The solid-phase extraction cartridge that had loaded the nitrogen-containing organic matter was rinsed with 5 times the column volume of ultrapure water acidified to pH 2. Nitrogen was blown into the solid-phase extraction cartridge to remove the remaining water. The nitrogen-containing organic matter was eluted from the solid-phase extraction cartridge with 3 times the column volume of LC-MS grade methanol at a flow rate of 1.5 mL/min. Prior to analysis on an instrument, the concentration of dissolved organic carbon in the wastewater sample was measured to be 50-100 mg/L.

2) The nitrogen-containing organic matter was detected and analyzed by a Fourier-transform ion cyclotron resonance mass spectrometer, thereby obtaining mass spectra of the nitrogen-containing organic matter. The operating parameters for the Fourier-transform ion cyclotron resonance mass spectrometer were as follows: the mass spectrometry was equipped with an electrospray ionization source, operated in negative ion mode, at a sampling rate of 180 μL/h, at a polarization voltage of 3.0 kV, at a DC voltage of 2.2 V, and using an accumulation time of 0.001 s. The mass of the collected molecules was in the range of 180-1000 Da and the number of sampling points was 3 M. The mass spectrum of the peak corresponding to the nitrogen-containing organic matter was a spectrum superimposed 260 times.

3) The mass of nitrogen-containing organic matter that corresponds to the peak in the mass spectrum was calibrated according to the IUPAC calibration table, and the error range of the mass was ±1 ppm. A method for calculating the molecular formula of the nitrogen-containing organic matter corresponding to the peak in the mass spectrum: the peak corresponding to the nitrogen-containing organic matter that had a signal-to-noise ratio greater than 6 was processed with the high-resolution mass spectrometry software; the molecular formula was calculated according to the ultra-high-precision mass-to-charge ratio of the peak corresponding to the nitrogen-containing organic matter. For each molecular formula, the number of carbon atoms was $2 \leq C \leq 50$, the number of hydrogen atoms was $2 \leq H \leq 120$ and $2 \leq H \leq 2C+2$, the number of oxygen atoms was $0 \leq O \leq 30$ and $0 \leq O \leq C+2$, the number of nitrogen atoms was $0 \leq N \leq 6$, $N < O$ and $N/C \leq 0.5$, the number of sulfur atoms was $0 \leq S \leq 2$, $S < O$ and $S/C \leq 0.2$, and the number of phosphorus atoms was $0 \leq P \leq 2$, $P/C \leq 0.1$ and $(2S+P) < O$. The number of equivalent double bonds was an integer greater than or equal to 0 (The formula for calculating the equivalent double bond was as follows: equivalent double bond=C—H/2+N/2+1). The nitrogen-containing organic molecules after pretreatment were set as global variables. According to the wastewater treatment process, the wastewater samples were arranged into cross-sectional data $G=\{W^t \in R^{n \times p}, t=1, 2, \ldots, T-1, T\}$, $W^t$ was the set of variables in the 4 wastewater treatment processes of n wastewater treatment plants, comprising influent tank, anoxic tank, aerobic tank, and effluent tank. $f_1$, $f_2$, $f_3$, $f_4$, $f_5$, $f_6$, and $f_7$ represent different wastewater treatment plants. $f_1^t$, $f_2^t$, $f_3^t$, $f_4^t$, $f_5^t$, $f_6^t$, and $f_7^t$ represent the set of molecular formulas of nitrogen-containing organic matter in the t wastewater treatment processes of different wastewater treatment plants. The intensities of the peaks corresponding to the molecular formulas of nitrogen-containing organics of the different wastewater treatment plants were $e_1^t$, $e_2^t$, $e_3^t$, $e_4^t$, $e_5^t$, $e_6^t$, and $e_7^t$. The cluster point of the t wastewater treatment process of the wastewater treatment plant was $L^t=\{f_n^t, i=1, 2, \ldots, n\}$. The cluster point of the global sewage water sample was $L=\cup_{t=1}^{T} L^t$. The global molecular formulas of nitrogen-containing organic matter were as follows: $f_{1m}^1$, $f_{2m}^1$, $f_{3m}^1$, $f_{4m}^1$, $f_{5m}^1$, $f_{6m}^1$, $f_{7m}^1$; $f_{1m}^2$, $f_{2m}^2$, $f_{3m}^2$, $f_{4m}^2$, $f_{5m}^2$, $f_{6m}^2$, $f_{7m}^2$; $f_{1m}^t$, $f_{2m}^t$, $f_{3m}^t$, $f_{4m}^t$, $f_{5m}^t$, $f_{6m}^t$, $f_{7m}{}^t$. The cross-sectional data was used to create an assessment matrix for evaluating the removal of nitrogen-containing organic matter in the effluent of the wastewater treatment plant. The assessment matrix was input into a statistical analysis software to establish an unsupervised dimensionality reduction analysis system.

4) The inverse index was homogenized with reciprocal method. Standard deviation and logarithm were used to standardize the intensities of the peaks in the mass spectrum that correspond to the molecular formulas of all nitrogen-containing organic matter. The Kaiser-Meyer-Olkin (KMO) test and Bartlett's test were used to determine the correlation between global variables in the unsupervised dimensionality reduction analysis system. The covariance matrix of the global variable was calculated using the standardized peak intensity of the nitrogen-containing organic molecules that are homogenized and globally standardized.

5) The covariance matrix of global variables was used to calculate the eigenvalues, variance contribution rate of the eigenvalues, eigenvectors, cumulative variance contribution rate, global principal components, and comprehensive score of each wastewater treatment process of each wastewater sewage plant (The global principal component should satisfy the condition that the eigenvalue was greater than 1). A score for the removal of nitrogen-containing organic matter in each wastewater treatment process was calculated with the unsupervised feature reduction technique. The score for the removal of nitrogen-containing organic matter from each wastewater treatment process of the wastewater treatment plant was calculated according to the sum of the product of the score of each wastewater treatment process in each global principal component and the contribution rate of the corresponding variance. The score is sorted in order, thereby evaluating the effect of removal of the nitrogen-containing organic matter in each wastewater treatment plant and each wastewater treatment process.

TABLE 4

Score and rank of the removal effect of nitrogen-containing organic matter in the influent and effluent of wastewater treatment plants

| Municipal wastewater treatment plant | Influent | | Anoxic tank | | Aerobic tank | | Effluent | |
|---|---|---|---|---|---|---|---|---|
| | Score | Rank | Score | Rank | Score | Rank | Score | Rank |
| f1 | −0.041 | 5 | 0.087 | 4 | 0.514 | 3 | 0.455 | 2 |
| f2 | −0.622 | 6 | −0.292 | 5 | −0.053 | 5 | 0.195 | 4 |
| f3 | 0.889 | 2 | 0.813 | 2 | −0.989 | 7 | −1.008 | 7 |
| f4 | −1.174 | 7 | 1.001 | 1 | 0.859 | 1 | 0.976 | 1 |
| f5 | 0.493 | 3 | −0.620 | 6 | 0.347 | 4 | 0.299 | 3 |
| f6 | 0.483 | 4 | 0.176 | 3 | 0.555 | 2 | −0.251 | 5 |
| f7 | 1.096 | 1 | −0.983 | 7 | −0.387 | 6 | −0.815 | 6 |

The effect of removal of nitrogen-containing organic matter was ranked and evaluated by score. The scores in Table 4 were calculated using the molecular composition of nitrogen-containing organic matter in the wastewater and the matrix of intensities of peaks corresponding to the nitrogen-containing organic matter. The higher the score, the higher the rank, and the more the serious pollution/the worse the removal effect caused by the nitrogen-containing organic matter in the wastewater. In the 7 municipal wastewater treatment plants, the pollution degree of nitrogen-containing organic matter in the influent. f7>f3>f5>f6>f1>f2>f4; the effect of removal of nitrogen-containing organic matter in the aerobic tank: f7>f5>f2>f1>f6>f3>f4; the effect of removal of nitrogen-containing organic matter in the aerobic tank: f3>f7>f2>f5>f1>f6>f4; the contribution rate of nitrogen-containing organic matter was defined as the standard, and the cleanliness of the effluent was ranked as f3>f7>f6>f2>f5>f1>f4. According to the ranking, the effect of removal of nitrogen-containing organic matter in the municipal wastewater treatment plant f1 was lower than that of other wastewater treatment plants. The effect of removal of nitrogen-containing organic matter in the aerobic tank of the municipal wastewater treatment plant f4 was lower than that of other wastewater treatment plants. The effects of removal of nitrogen-containing organic matter in the municipal wastewater treatment plants f3 and f7 were more stable than that of other wastewater treatment plants.

It will be obvious to those skilled in the art that changes and modifications may be made, and therefore, the aim in the appended claims is to cover all such changes and modifications.

What is claimed is:
1. A method, comprising:
   1) pretreating a wastewater sample from a wastewater treatment plant; enriching nitrogen-containing organic matter in the wastewater sample with a solid-phase extraction cartridge; using a solid-phase extraction cartridge to separate the nitrogen-containing organic matter from a substrate and disruptors of the enriched wastewater sample through operations comprising column activation, sample loading, column rinsing, and column elution, and collecting the nitrogen-containing organic matter from the eluted wastewater sample;
   2) detecting and analyzing the nitrogen-containing organic matter collected in 1) with a Fourier-transform ion cyclotron resonance mass spectrometer, thereby obtaining mass spectra of the nitrogen-containing organic matter;
   3) preprocessing peak data of the mass spectra of the nitrogen-containing organic matter in each wastewater sample; setting the nitrogen-containing organic matter corresponding to the peak data as a global variable; arranging wastewater samples into cross-sectional data according to wastewater treatment processes; creating an assessment matrix for evaluating removal of the nitrogen-containing organic matter from the wastewater treatment plant; inputting the assessment matrix into a statistical analysis software, thereby establishing an unsupervised dimensionality reduction analysis system;
   4) homogenizing and standardizing global variables in the unsupervised dimensionality reduction analysis sys- tem; summarizing a correlation between two global variables with a multivariate statistical method; computing a covariance matrix of the global variables; and 5) calculating, based on the covariance matrix of the global variables, a score for estimating the removal of nitrogen-containing organic matter in the unsupervised dimensionality reduction analysis system corresponding to each wastewater treatment process; sorting scores in order; evaluating the effect of the removal of the nitrogen-containing organic matter from each wastewater treatment plant and each wastewater treatment process according to sorted scores.

2. The method of claim 1, wherein the wastewater treatment plant is a municipal wastewater treatment plant or an industrial wastewater treatment plant; the wastewater treatment process comprises primary water treatment, secondary water treatment, and tertiary water treatment; when evaluating the effect of removal of nitrogen-containing organic matter, wastewater treatment processes of different wastewater treatment plants are of one type.

3. The method of claim 1, wherein
in 1), the wastewater sample is pretreated through a cellulose acetate membrane having a pore size of 0.45 μm to remove particles and bacteria, and a pH of the wastewater sample is adjusted to 2 with American Chemical Society (ACS)-grade high-purity hydrochloric acid;
the solid-phase extraction cartridge is a solid-phase extraction cartridge with styrene-divinylbenzene copolymer as a filler;
column activation comprises: removing impurities in the solid-phase extraction cartridge with 2-3 times the column volume of LC-MS grade methanol, and equilibrating the solid-phase extraction cartridge with 3-5 times the column volume of ultrapure water acidified to pH 2;
the wastewater sample is loaded onto the solid-phase extraction cartridge, with a flow rate of 0.5-2 mL/min;
column rinsing comprises: rinsing the solid-phase extraction cartridge loaded with the nitrogen-containing organics with 3 times the column volume of ultrapure water acidified to pH 2, blowing nitrogen into the solid-phase extraction cartridge to remove remaining water, eluting the nitrogen-containing organics from the solid-phase extraction cartridge with 1-3 times the column volume of LC-MS grade methanol at a flow rate of 0.5-1.5 mL/min; and
prior to analyzing the nitrogen-containing organic matter collected in 1) a concentration of dissolved organic carbon in the wastewater sample is 50-100 mg/L.

4. The method of claim 3, wherein the ultrapure water acidified to pH 2 is LC-MS grade ultrapure water acidified by ACS grade high-purity hydrochloric acid.

5. The method of claim 1, wherein in 2), operating parameters for the Fourier-transform ion cyclotron resonance mass spectrometer are as follows: the mass spectrometer is equipped with an electrospray ionization source, operating in negative ion mode, at a sampling rate of 120-180 μL/h, a polarization voltage of 2.5-3.0 kV, a DC voltage of 2.2-2.4 V, and an accumulation time of 0.001-0.1 s; a mass of collected molecules is in the range of 180-1000 Da and a number of sampling points is 2-4 M; and a mass spectrum of a peak corresponding to the nitrogen-containing organic matter is a spectrum superimposed by 230-260 times.

6. The method of claim 1, wherein in 3), preprocessing peak data comprises calibrating a mass of nitrogen-containing organic matter that corresponds to a peak in the mass spectrum according to the IUPAC calibration table, and an error range of the mass is ±1 ppm; calculating a molecular formula of the nitrogen-containing organic matter that corresponds to the peak in the mass spectrum comprises: processing the peak corresponding to the nitrogen-containing organic matter that has a signal-to-noise ratio greater than 6 with a high-resolution mass spectrometry software; calculating the molecular formula according to an ultra-high-precision mass-to-charge ratio of the peak corresponding to the nitrogen-containing organic matter; for each molecular formula, a number of carbon atoms is $2 \leq C \leq 50$, a number of hydrogen atoms is $2 \leq H \leq 120$ and $2 \leq H \leq 2C+2$, a number of oxygen atoms is $0 \leq O \leq 30$ and $0 \leq O \leq C+2$, a number of nitrogen atoms is $0 \leq N \leq 6$, $N < O$ and $N/C \leq 0.5$, a number of sulfur atoms is $0 \leq S \leq 2$, $S < O$ and $S/C \leq 0.2$, and a number of phosphorus atoms is $0 \leq P \leq 2$, $P/C \leq 0.1$ and $(2S+P) < O$, and an equivalent double bond is an integer greater than or equal to 0; the cross-sectional data is as follows: $G = \{W^t \in R^{n \times p}, t=1, 2, \ldots, T-1, T\}$, $W^t$ is a set of variables in t wastewater treatment processes of n wastewater treatment plants. $f_1, f_2, \ldots, f_n$ represent different wastewater treatment plants. $f_1^t, f_2^t, \ldots, f_n^t$ represent a set of molecular formulas of nitrogen-containing organic matter in the t process unit of different wastewater treatment plants; intensities of the peaks corresponding to the molecular formulas of nitrogen-containing organic matter of the wastewater treatment plants are $e_1^t, e_2^t, \ldots, e_n^t$; a cluster point of the t wastewater treatment process of the wastewater treatment plant is $L^t = \{f_n^t, i=1, 2, \ldots, n\}$; a cluster point of the global sewage water sample is $L = U_{t=1}^T L^t$; and a global molecular formulas of nitrogen-containing organic matter are as follows: $f_{1m}^1, \ldots, f_{nm}^1; f_{1m}^2, \ldots, f_{nm}^2; \ldots; f_{1m}^t, \ldots, f_{nm}^t$.

7. The method of claim 6, wherein the equivalent double bond is calculated as follows: equivalent double bond=$C-H/2+N/2+1$.

8. The method of claim 1, wherein in 4), homogenizing comprises calculating a reciprocal of an inverse index; standardizing comprises calculating a standard deviation and logarithm of the intensities of the peaks corresponding to the molecular formula of all nitrogen-containing organic matter in the mass spectrum; the multivariate statistical method comprises Kaiser-Meyer-Olkin (KMO) test and Bartlett's test among variables; calculating the covariance matrix comprises homogenizing and globally standardizing the intensities of the peaks corresponding to the molecular formulas of the nitrogen-containing organic matter.

9. The method of claim 1, wherein in 5), calculating the score for estimating the removal of nitrogen-containing organic matter comprises calculating eigenvalue, variance contribution rate of the eigenvalue, eigenvector, cumulative variance contribution rate, global principal components, and comprehensive score of each wastewater treatment plant.

10. The method of claim 9, wherein the global principal component satisfies the condition that the eigenvalue is greater than 1; the score of each wastewater treatment process of each wastewater treatment plant is a sum of a product of the global principal component scores and their corresponding variance contribution rates.

* * * * *